(12) United States Patent
Fields et al.

(10) Patent No.: US 9,435,801 B2
(45) Date of Patent: Sep. 6, 2016

(54) SYSTEMS AND METHODS TO MANAGE ZOOMING

(75) Inventors: Gregory Jason Fields, Waterloo (CA); Laura Ann Mahan, Kanata (CA)

(73) Assignee: BlackBerry Limited, Waterloo, Ontario (CA)

(*) Notice: Subject to any disclaimer, the term of this patent is extended or adjusted under 35 U.S.C. 154(b) by 217 days.

(21) Appl. No.: 13/634,930

(22) PCT Filed: May 18, 2012

(86) PCT No.: PCT/CA2012/050329
§ 371 (c)(1),
(2), (4) Date: Sep. 14, 2012

(87) PCT Pub. No.: WO2013/170341
PCT Pub. Date: Nov. 21, 2013

(65) Prior Publication Data
US 2013/0311941 A1    Nov. 21, 2013

(51) Int. Cl.
*G06T 3/40* (2006.01)
*G01N 33/543* (2006.01)
(Continued)

(52) U.S. Cl.
CPC ......... *G01N 33/54346* (2013.01); *B82Y 30/00* (2013.01); *C07H 21/00* (2013.01); *C12Q 1/6816* (2013.01); *C12Q 1/6825* (2013.01);
(Continued)

(58) Field of Classification Search
CPC ........... H04N 3/1562; H04N 5/23296; H04N 5/2628; G06F 2203/04805; G06F 2203/04806; G06F 2203/04808; G06F 3/0481; G06F 3/0485; G06F 3/04883; G06T 3/40

USPC ........ 715/744–747, 800–807, 848, 850–855, 715/863–866; 382/298
See application file for complete search history.

(56) References Cited

U.S. PATENT DOCUMENTS 5,940,077 A * 8/1999 Amro ............................ 715/800
7,487,447 B1 * 2/2009 Jerger ........................... 715/252
(Continued)

FOREIGN PATENT DOCUMENTS

| CA | 2711287 A1 | 3/2011 |
| WO | WO2010144201 A2 | 12/2010 |
| WO | WO2012007745 A2 | 1/2012 |

OTHER PUBLICATIONS

Tackaberry, "NoSquint", Dec. 24, 2010, https://urandom.ca/nosquint and https://urandom.ca/nosquinthelp.php, p. 1-4.*
(Continued)

*Primary Examiner* — Tadeese Hailu
*Assistant Examiner* — Alvaro R Calderon, IV
(74) *Attorney, Agent, or Firm* — Jeffrey N. Giunta; Fleit Gibbons Gutman Bongini & Bianco P.L.

(57) ABSTRACT

Systems and methods are provided to manage zooming in an electronic device. An example embodiment method includes receiving an input to increase or decrease a zoom level in an application. If it is determined the application includes a local zoom functionality, then it is further determined if a global zoom functionality is turned on. If so, the global zoom is turned off and then the local zoom is used to increase or decrease the zoom level. In another example embodiment, a method includes receiving an input to activate global zoom. If it is determined the global zoom is turned on, then the global zoom is activated.

21 Claims, 15 Drawing Sheets

(51) Int. Cl.

| | | |
|---|---|---|
| *B82Y 30/00* | (2011.01) | |
| *C07H 21/00* | (2006.01) | |
| *C12Q 1/68* | (2006.01) | |
| *G01N 33/532* | (2006.01) | |
| *G01N 33/533* | (2006.01) | |
| *G01N 33/58* | (2006.01) | |

(52) U.S. Cl.
CPC ........... *C12Q1/6834* (2013.01); *G01N 33/532* (2013.01); *G01N 33/533* (2013.01); *G01N 33/5438* (2013.01); *G01N 33/54306* (2013.01); *G01N 33/54366* (2013.01); *G01N 33/582* (2013.01); *G01N 33/587* (2013.01); *C07B 2200/11* (2013.01); *G01N 2458/30* (2013.01)

(56) References Cited

U.S. PATENT DOCUMENTS

| | | | |
|---|---|---|---|
| 7,705,864 | B2 | 4/2010 | Ahmed et al. |
| 7,916,157 | B1* | 3/2011 | Kelley et al. ................. 345/660 |
| 8,307,279 | B1* | 11/2012 | Fioravanti et al. .......... 715/243 |
| 8,427,445 | B2* | 4/2013 | Kennedy ...................... 345/173 |
| 8,493,344 | B2* | 7/2013 | Fleizach et al. ............. 345/173 |
| 8,744,852 | B1* | 6/2014 | Seymour et al. ............ 704/260 |
| 8,928,700 | B1* | 1/2015 | Khafizova ................... 345/661 |
| 2003/0214519 | A1* | 11/2003 | Smith et al. ................. 345/660 |
| 2005/0001815 | A1* | 1/2005 | Tsunoda ...................... 345/158 |
| 2005/0012723 | A1 | 1/2005 | Pallakoff |
| 2005/0195221 | A1* | 9/2005 | Berger et al. ................ 345/660 |
| 2006/0026170 | A1* | 2/2006 | Kreitler et al. ................ 707/10 |
| 2006/0050090 | A1* | 3/2006 | Ahmed et al. ................ 345/660 |
| 2006/0111634 | A1* | 5/2006 | Wu ................................ 600/443 |
| 2006/0197782 | A1* | 9/2006 | Sellers et al. ................ 345/660 |
| 2007/0033542 | A1* | 2/2007 | Winser et al. ............... 715/788 |
| 2007/0033543 | A1* | 2/2007 | Ngari et al. .................. 715/788 |
| 2007/0035658 | A1* | 2/2007 | Ketterer et al. ............. 348/375 |
| 2007/0268317 | A1* | 11/2007 | Banay .......................... 345/660 |
| 2008/0062202 | A1* | 3/2008 | Schulz et al. ................ 345/665 |
| 2008/0074511 | A1* | 3/2008 | Kramp et al. .............. 348/240.3 |
| 2008/0168402 | A1* | 7/2008 | Blumenberg ................ 715/863 |
| 2008/0253757 | A1* | 10/2008 | Bells et al. ...................... 396/77 |
| 2009/0109243 | A1* | 4/2009 | Kraft et al. .................. 345/660 |
| 2009/0167509 | A1 | 7/2009 | Fadell et al. |
| 2009/0322497 | A1* | 12/2009 | Ku et al. .................... 340/407.2 |
| 2010/0017740 | A1* | 1/2010 | Gonzalez Veron et al. .. 715/777 |
| 2010/0031169 | A1* | 2/2010 | Jang et al. ................... 715/760 |
| 2010/0079498 | A1* | 4/2010 | Zaman et al. ............... 345/661 |
| 2010/0083186 | A1* | 4/2010 | Zaman et al. ............... 715/856 |
| 2010/0085384 | A1* | 4/2010 | Kim et al. ................... 345/660 |
| 2010/0169766 | A1* | 7/2010 | Duarte et al. ............... 715/244 |
| 2010/0223577 | A1* | 9/2010 | Bennett et al. .............. 715/800 |
| 2010/0235736 | A1* | 9/2010 | Fleisher et al. ............. 715/702 |
| 2010/0309147 | A1* | 12/2010 | Fleizach et al. ............. 345/173 |
| 2010/0309148 | A1* | 12/2010 | Fleizach et al. ............. 345/173 |
| 2010/0313125 | A1* | 12/2010 | Fleizach et al. ............. 715/702 |
| 2011/0035702 | A1* | 2/2011 | Williams et al. ............ 715/800 |
| 2011/0072390 | A1* | 3/2011 | Duga et al. .................. 715/800 |
| 2011/0119289 | A1 | 5/2011 | Fields et al. |
| 2011/0161871 | A1* | 6/2011 | Stringer et al. ............. 715/800 |
| 2011/0221745 | A1* | 9/2011 | Goldman et al. ........... 345/419 |
| 2011/0244954 | A1* | 10/2011 | Goldman et al. ............. 463/30 |
| 2011/0249032 | A1* | 10/2011 | Bells et al. .................. 345/660 |
| 2011/0252302 | A1* | 10/2011 | Yalovsky ..................... 715/234 |
| 2011/0252335 | A1* | 10/2011 | Lloyd et al. ................. 715/744 |
| 2011/0283227 | A1* | 11/2011 | Moore et al. ................ 715/800 |
| 2012/0001914 | A1* | 1/2012 | Pan et al. ..................... 345/428 |
| 2012/0042236 | A1 | 2/2012 | Adler, III et al. |
| 2012/0092277 | A1* | 4/2012 | Momchilov ................. 345/173 |
| 2012/0257072 | A1* | 10/2012 | Jirman ....................... 348/222.1 |
| 2012/0306930 | A1* | 12/2012 | Decker et al. ............... 345/667 |
| 2012/0317522 | A1* | 12/2012 | Duarte et al. ............... 715/863 |
| 2013/0067391 | A1* | 3/2013 | Pittappilly et al. ........... 715/784 |
| 2013/0125068 | A1* | 5/2013 | Harris et al. ................ 715/863 |
| 2013/0132867 | A1* | 5/2013 | Morris et al. ............... 715/759 |
| 2013/0185164 | A1* | 7/2013 | Pottjegort .................. 705/14.73 |
| 2013/0198641 | A1* | 8/2013 | Brownlow et al. .......... 715/738 |
| 2013/0311921 | A1* | 11/2013 | Fleizach et al. ............. 715/767 |

OTHER PUBLICATIONS

Robertson, George G. and Mackinlay, Jock D. "The Document Lens" UIST '93, Nov. 3-5, 1993, pp. 101-108, Atlanta, ACM #0-089791-628-X/93/0011.*

"iPhone User Guide", Mar. 9, 2011, Apple Inc., https://manuals.info.apple.com/MANUALS/1000/MA1539/en_US/iPhone_iOS4_User_Guide.pdf.*

Kline, Richard L. and Glinert, Ephraim P. "Improving GUI Accessibility for People with Low Vision," Proceedings of the SIGCHI Conference on Human Factors in Computing Systems, May 7-11, 1995, pp. 114-121, Denver.*

Simkovits, Daniel "LP-DOS Magnifies the PC Screen," 1992, p. 203-204, IEEE #0-8186-2730-1/92.*

Bartlett, M., "iPhone & iPad: Enable or Disable Zoom", Oct. 4, 2014, http://www.technipages.com/iphone-enable-disable-zoom.*

Tackaberry (Dec. 1, 2010): NoSquint, p. 1-6. Date verified using waybackmachine: http://web.archive.org/web/20101201091618/https://urandom.ca/nosquint/help.php.

Johansson (May 19, 2011): iOS tip: how to zoom on web pages that have disabled user zoom. p. 1. Date verified using waybackmachine: http://web.archive.org/web/20110519233630/http://www.456bereastreet.com/archive/201105/ios_tip_how_to_zoom_on_web_pages_that_have_disabled_user_zoom/.

Khoury, Tony; International Search Report from correspnoding PCT Application No. PCT/CA2012/050329; search completed Aug. 28, 2012.

* cited by examiner

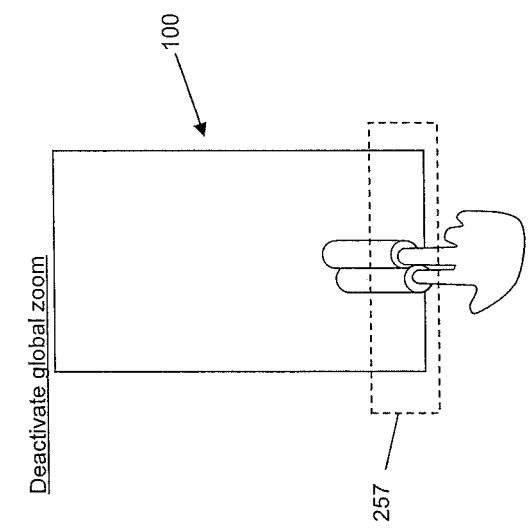
Figure 15
Figure 16
Figure 17

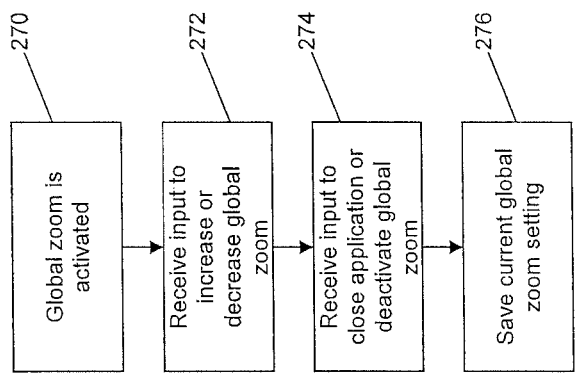

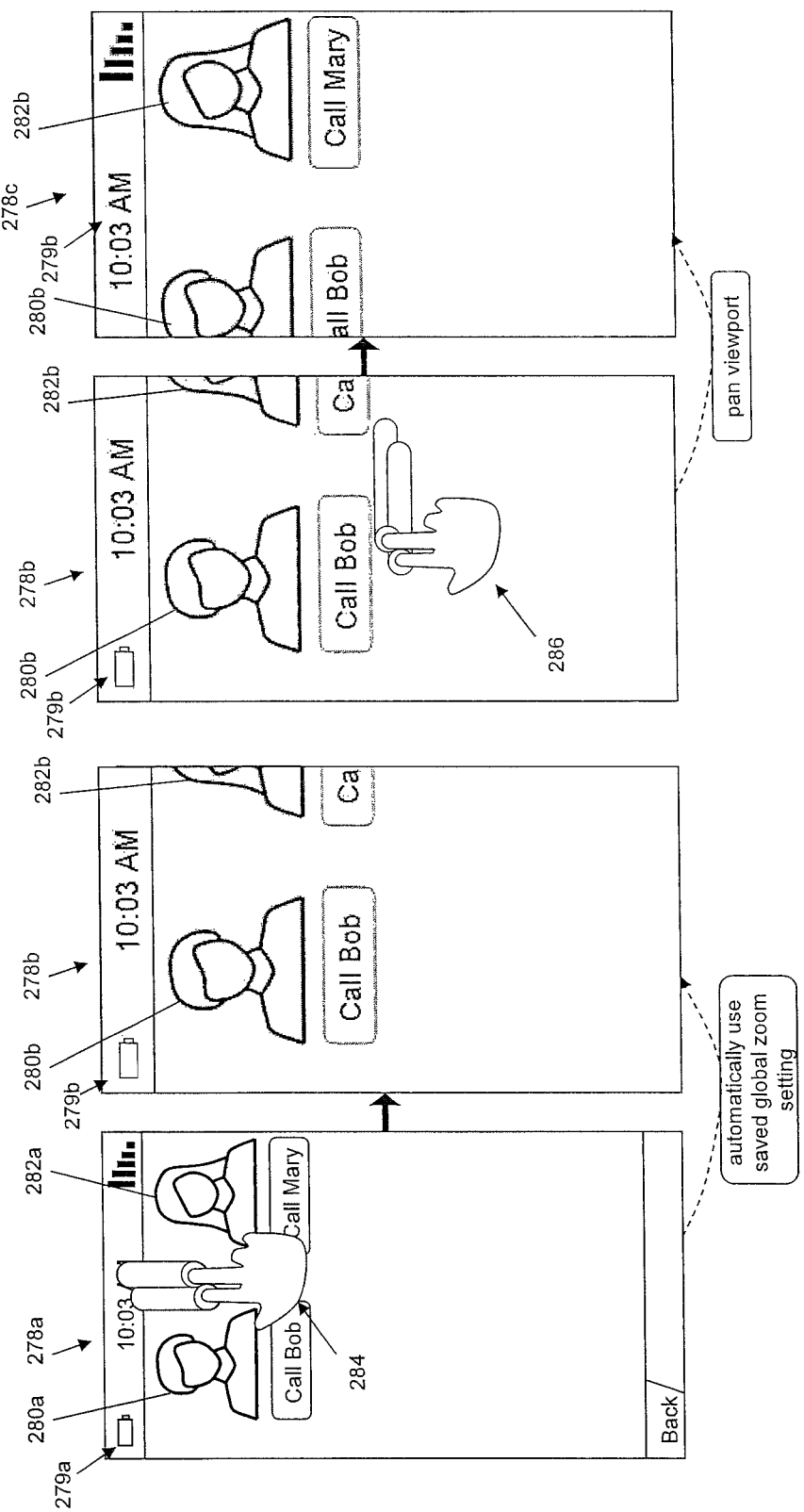

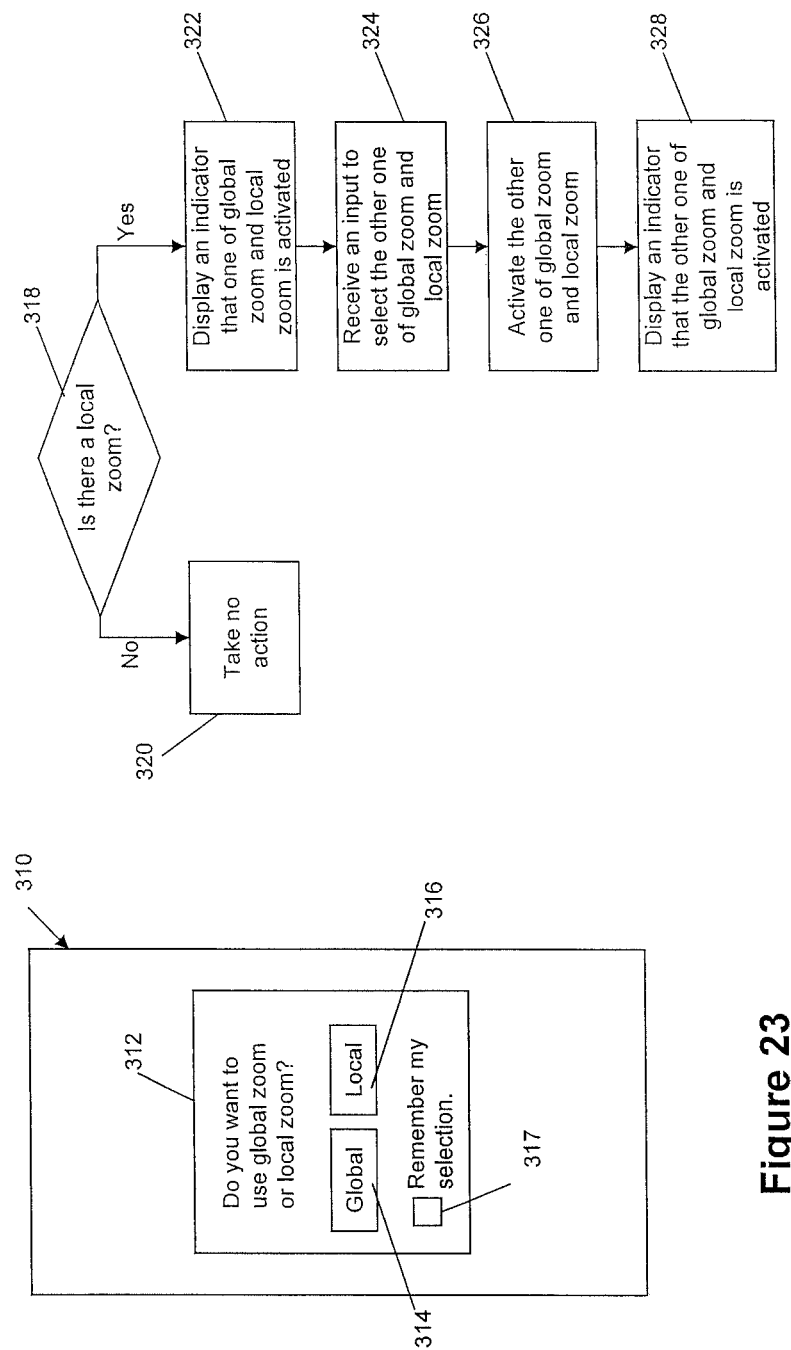

SYSTEMS AND METHODS TO MANAGE ZOOMING

TECHNICAL FIELD

The following relates generally to managing zooming.

DESCRIPTION OF THE RELATED ART

Many electronic devices, including mobile devices, include applications. An application may have a zoom feature. In some cases a zoom feature is not provided. Generally, zooming refers to increasing or decreasing the scale of a viewed area on the electronic device in order to see more detail or less. For example, if an image or if text is too small to see, then a user can zoom into the image or text, thereby increasing the image size or text size being displayed on the electronic device.

BRIEF DESCRIPTION OF THE DRAWINGS

Example embodiments will now be described by way of example only with reference to the appended drawings wherein:

FIG. 15 is an example embodiment of a touch screen gesture for panning a viewport.

FIG. 16 is an example embodiment of a touch screen gesture for deactivating global zoom.

FIG. 17 is a flow diagram of computer executable or processor implemented instructions for activating global zoom according to a saved global zoom setting.

FIG. 18 is a flow diagram of computer executable or processor implemented instructions for saving the global zoom setting.

FIG. 19 is an illustration of example embodiment screen shots for activating global zoom according to the saved global zoom setting.

FIG. 20 is an illustration of example embodiment screen shots for panning a viewport while global zoom is activated.

FIG. 23 is a screen shot of an example embodiment prompt used to determine if a user would like to use global zoom or local zoom.

FIG. 24 is a flow diagram of computer executable or processor implemented instructions for selecting global zoom or local zoom.

DETAILED DESCRIPTION

Figure 1:
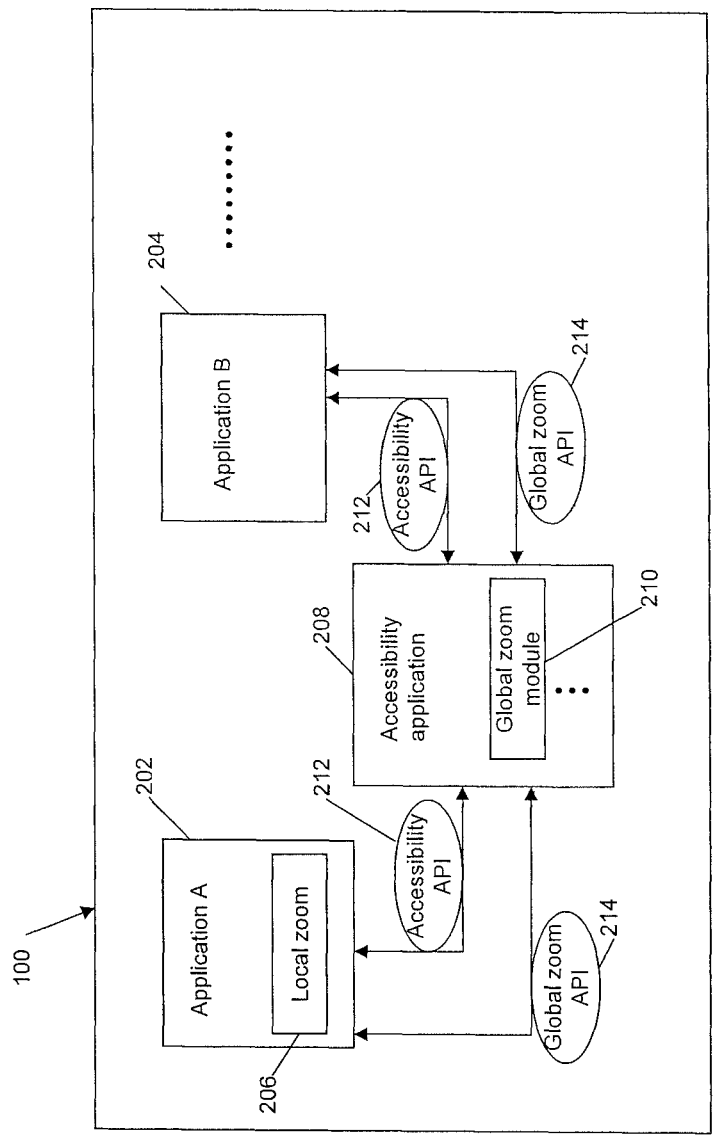
FIG. 1 is a block diagram of an example embodiment of an electronic device for managing zooming.

It will be appreciated that for simplicity and clarity of illustration, where considered appropriate, reference numerals may be repeated among the example figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures and components have not been described in detail so as not to obscure the example embodiments described herein. Also, the description is not to be considered as limiting the scope of the example embodiments described herein.

For the purposes of the present description, "assistive technology" or an "assistive technology application" is an application that may be used on an electronic device to assist a user in interacting with the electronic device. For example, a screen reader is an assistive technology application. Screen magnifiers, self-voicing applications, and customized graphical user interfaces to alter colors and sizes of desktops, short-cut icons, menu bars, and scroll bars are other examples. Yet other examples are optical character recognition to convert the printed word into text via a scanner, Braille translation to convert the printed word into Braille, text-to-speech, speech-to-text, spell checkers, and grammar checkers. Assistive technology may be used to assist users dealing with blindness, vision impairment, colorblindness, deafness, hearing impairment, speech impairment, motor impairments, and cognitive or learning disabilities.

Applications compatible with assistive technology applications are also known as accessible applications. Accessible applications work with assistive technology applications to provide the feature offered by the assistive technology for the given accessible application.

An electronic device having a display screen, or connected to a display screen, can be used to control the zooming of images being displayed. Zooming generally refers to increasing or decreasing the scale of a viewed area on the electronic device in order to see more detail or less.

In an example embodiment, applications on the electronic device may have their respective zooming capabilities. These are herein referred to as "local zoom". For example, a game application on an electronic device has local zoom capabilities. As a user zooms into a scene or an image of the game, graphics rendering may be used to increase the size of objects and show the objects in greater detail. In an example embodiment, a local zoom action is only particular to some of the content. In an example embodiment, the local zoom does not increase or decrease the zooming or zoom level on other content.

For example, the content displayed by a game application includes graphics for a virtual world and user controls for navigating within the virtual world. A user can use local zoom to zoom into the graphics for the virtual world, but the controls will remain the same size. In other words, the local zoom does not affect the size of the controls.

It is recognized that users may desire to have all content displayed on a screen to be increased or decreased in size. For example, a user may wish to zoom into the controls of the game application to better view the controls. The controls, for example, can be too small to see and, thus, difficult to determine their meaning.

In an example embodiment, an electronic device includes global zoom functionality. Global zoom refers to an ability to zoom in on all content displayed on a screen. In an example embodiment, global zoom can be applied to all applications and, thus, can be used to supplement or replace local zoom.

For example, some applications on an electronic device do not have local zoom. Global zoom can be used with such applications to increase or decrease the zoom level.

In an example embodiment, the zoom level refers to a percentage of increase or decrease of size compared to the original image size. For example, a zoom level of 200% represents "zooming in" to the image so that the image is twice as large as the original image. A zoom level of 50% represents "zooming out" of the image so that the image is half the size as the original image.

It is recognized that managing the use of global zoom and local zoom can be difficult, including determining when and how to employ one of global and local zoom in an application.

The systems and methods described herein address issues related to managing zooming.

Turning to FIG. 1, an example embodiment of an electronic device 100 is provided. It includes an accessibility application 208, which further includes a global zoom module 210.

In some example embodiments, the accessibility application 208 has the ability to send and receive data items via a wireless network. In some example embodiments, information is provided on an external server (not shown) and used by the accessibility application 208 which accesses the information through the wireless network. In an example embodiment, the accessibility application 208 has the ability to determine if a new application being launched is an accessible application, and if so, enable at least one assistive technology feature at launch of the application. The accessibility application 208 can also determine if assistive technology is present on the electronic device 100. In another example embodiment, it can also determine if an assistive technology is in use by the user of the electronic device. In another example embodiment, the accessibility application 208 is involved in the process of determining if the assistive technology feature should be enabled or disabled, and is involved in the process of the enablement or disablement.

An example embodiment of an assistive technology is zooming, as provided by the global zoom module 210. The global zoom module 210 facilitates global zooming for all content displayed on or by the electronic device 100. It can be appreciated that a display screen (not shown) can be integrated with the electronic device 100 or connected to the electronic device 100.

The electronic device 100 also includes applications. An example application 202 includes local zoom functionality 206. Another application 204 does not include local zoom functionality. The applications (e.g. 202, 204) interact with the accessibility application 208 and the global zoom module 210.

In an example embodiment, the applications (e.g. 202, 204) interact with the accessibility application 208 through an accessibility Application Programming Interface (API) 212. The accessibility API 212 allows the applications to provide information to the various assistive technology applications, including the global zoom module 210. In some example embodiments, the accessibility API 212 is not needed. For example, standard user interface components automatically provide information to assistive technology applications.

In an example embodiment, an application communicates with the accessibility application 208 to determine if global zoom is turned on or turned off. A message, which includes a value (e.g. Boolean value), is returned to the application which indicates whether global zoom is turned on or turned off.

If global zoom is used, the application interacts with the global zoom module 210 to increase or decrease the zoom, or zoom level.

In an example embodiment, the interaction between an application and the global zoom module 210 can occur through a global zoom API 214.

Example embodiments of mobile devices will now be described with reference to FIGS. 2 to 7.

It can be appreciated that various mobile devices can be used with the example embodiments described herein. Examples of applicable electronic devices include pagers, tablets, cellular phones, cellular smart-phones, wireless organizers, personal digital assistants, computers, laptops, handheld wireless communication devices, wirelessly enabled notebook computers, camera devices and the like. Such devices will hereinafter be commonly referred to as "mobile devices" for the sake of clarity. It will however be appreciated that the example embodiments described herein are also suitable for other devices, e.g. "non-mobile" devices. The non-mobile devices may include, for example, a desktop computer. More generally, both non-mobile and mobile devices are referred to as "electronic devices". Such terms can be interchangeable.

In an example embodiment, the mobile device is a two-way communication device with advanced data communication capabilities including the capability to communicate with other mobile devices or computer systems through a network of transceiver stations. The mobile device may also have the capability to allow voice communication. Depending on the functionality provided by the mobile device, it may be referred to as a data messaging device, a two-way pager, a cellular telephone with data messaging capabilities, a wireless Internet appliance, or a data communication device (with or without telephony capabilities).

Figure 3:
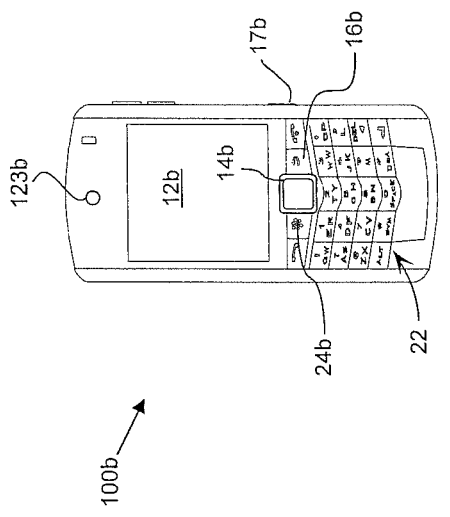
FIG. 3 is a plan view of another example embodiment mobile device.
Figure 2:
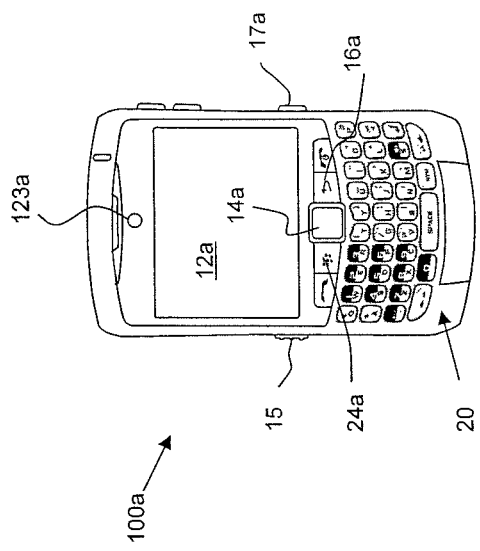
FIG. 2 is a plan view of an example embodiment mobile device.
Figure 4:
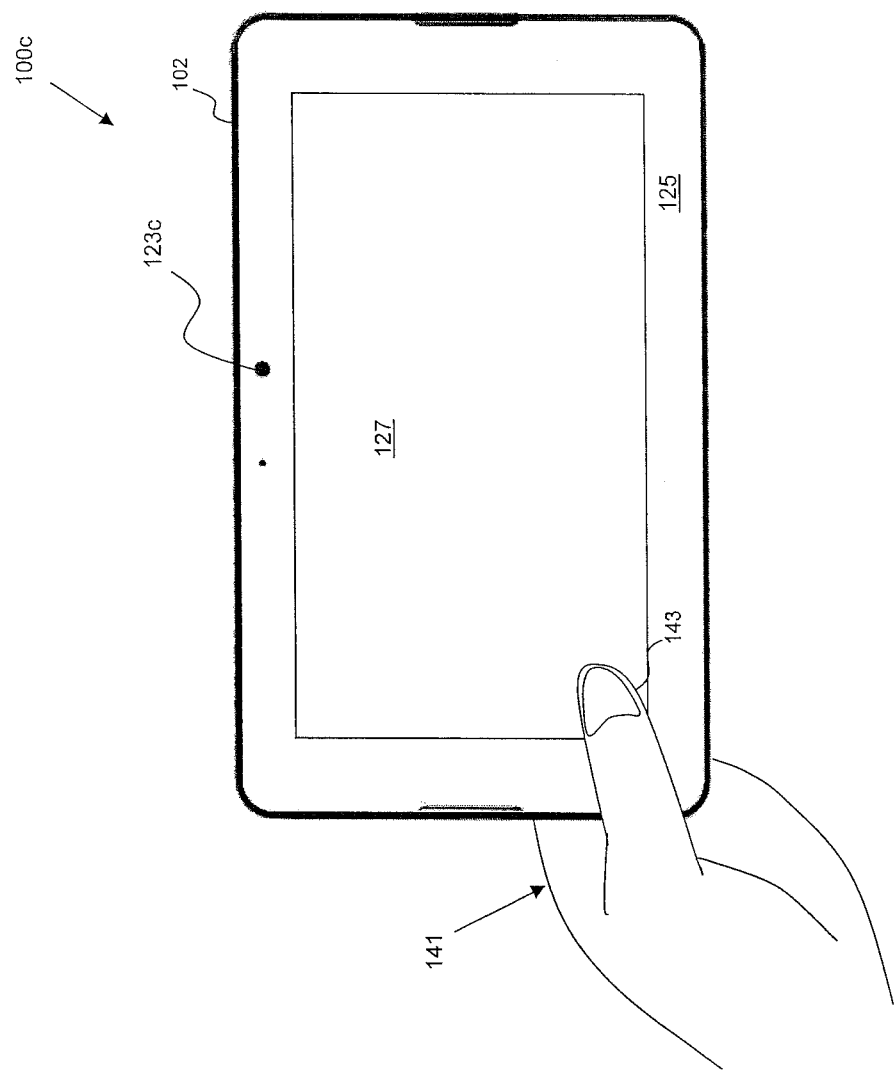
FIG. 4 is a plan view of another example embodiment mobile device.

Referring to FIGS. 2, 3 and 4, any of mobile devices 100a, 100b and 100c may be used to implement the example embodiments disclosed herein. It will be appreciated that the numeral "100" will hereinafter refer to any electronic device 100, including the example embodiments 100a, 100b and 100c, those example embodiments enumerated above or otherwise.

It will also be appreciated that for FIGS. 2 and 3, a similar numbering convention may be used for other general features common between FIGS. 2 and 3, such as a display 12, a positioning device 14, a cancel or escape button 16, a camera 123, a camera button 17, and a menu or option button 24.

The mobile device 100a shown in FIG. 2 includes a display 12a, a cursor or view positioning device 14, and a camera 123a. Shown in this example embodiment are a front-facing camera 123a and an optical track pad 14a. In another example embodiment, the positioning device 14 is a track ball (not shown). In yet another example embodiment, the camera 123a is a back-facing camera (not shown). Positioning device 14 may serve as another input member and detects the displacement of a finger that is moving on top of it to provide selection inputs to the main processor 102 (see FIG. 5). It can also be pressed in a direction generally toward housing to provide another selection input to the processor 102. The optical track pad 14a permits multi-directional positioning of the selection cursor 18 (see FIG. 6) such that the selection cursor 18 can be moved in an upward direction, in a downward direction and, if desired and/or permitted, in any diagonal direction. The optical track pad 14a is in this example situated on the front face of a housing for mobile device 100a as shown in FIG. 2 to enable a user to manoeuvre the optical track pad 14a while holding the mobile device 100a in one hand. The optical track pad 14a may serve as another input member (in addition to a directional or positioning member) to provide selection inputs to the processor 102 and can preferably be pressed in a direction towards the housing of the mobile device 100b to provide such a selection input.

The display 12a may include a selection cursor 18 that depicts generally where the next input or selection will be received. The selection cursor 18 may include a box, alteration of an icon or any combination of features that enable the user to identify the currently chosen icon or item. The mobile device 100a in FIG. 2 also includes a programmable convenience button 15 to activate a selected application such as, for example, a calendar or calculator. Further, mobile device 100a includes an escape or cancel button 16a, a camera button 17a, a menu or option button 24a and a keyboard 20. The camera button 17 is able to activate photo-capturing functions when pressed preferably in the direction towards the housing. The menu or option button 24 loads a menu or list of options on display 12a when pressed. In this example, the escape or cancel button 16a, the menu option button 24a, and keyboard 20 are disposed on the front face of the mobile device housing, while the convenience button 15 and camera button 17a are disposed at the side of the housing. This button placement enables a user to operate these buttons while holding the mobile device 100 in one hand. The keyboard 20 is, in this example embodiment, a standard QWERTY keyboard.

The mobile device 100b shown in FIG. 3 includes a display 12b, a camera 123b, and a cursor or view positioning device 14b. Shown in this example embodiment is a front-facing camera 123b and an optical track pad 14b. In another example embodiment, the positioning device 14b is a track ball (not shown). In yet another example embodiment, the camera 123b is a back-facing camera (not shown). The mobile device 100b also includes a menu or option button 24b, a cancel or escape button 16b, and a camera button 17b. The mobile device 100b as illustrated in FIG. 3 includes a reduced QWERTY keyboard 22. In this example embodiment, the keyboard 22, positioning device 14b, escape button 16b and menu button 24b are disposed on a front face of a mobile device housing. The reduced QWERTY keyboard 22 includes a plurality of multi-functional keys and corresponding indicia including keys associated with alphabetic characters corresponding to a QWERTY array of letters A to Z and an overlaid numeric phone key arrangement.

It will be appreciated that for the mobile device 100, a wide range of one or more positioning or cursor/view positioning mechanisms such as a touch pad, a positioning wheel, a joystick button, a mouse, a touch screen, a set of arrow keys, a tablet, an accelerometer (for sensing orientation and/or movements of the mobile device 100 etc.), or other whether presently known or unknown may be employed. Similarly, any variation of keyboard 20, 22 may be used. It will also be appreciated that the mobile devices 100 shown in FIGS. 2 and 3 are for illustrative purposes only and various other mobile devices 100 are equally applicable to the following examples. For example, other mobile devices 100 may include the trackball 14b, escape button 16b and menu or option button 24 similar to that shown in FIG. 3 only with a full or standard keyboard of any type. Other buttons may also be disposed on the mobile device housing such as colour coded "Answer" and "Ignore" buttons to be used in telephonic communications. In another example, the display 12 may itself be touch sensitive thus itself providing an input mechanism in addition to display capabilities.

The mobile device 100c shown in FIG. 4 includes a touch-sensitive display 102 and a front-facing camera 123. The touch-sensitive display 102 includes a touch-sensitive non-display area 125 surrounding a touch-sensitive display area 127, both of which may be capable of receiving inputs in the form of touch inputs. The front-facing camera 123 points towards the user of the mobile device 100c. Although not shown in FIG. 4, it can be appreciated that the mobile device 100c may also have a back-facing camera.

It can be appreciated that the devices shown in FIGS. 2 to 4 can have both a front-facing camera 123 and a back-facing camera.

To aid the reader in understanding the structure of the mobile device 100, reference will now be made to FIGS. 5 through 7.

Figure 5:
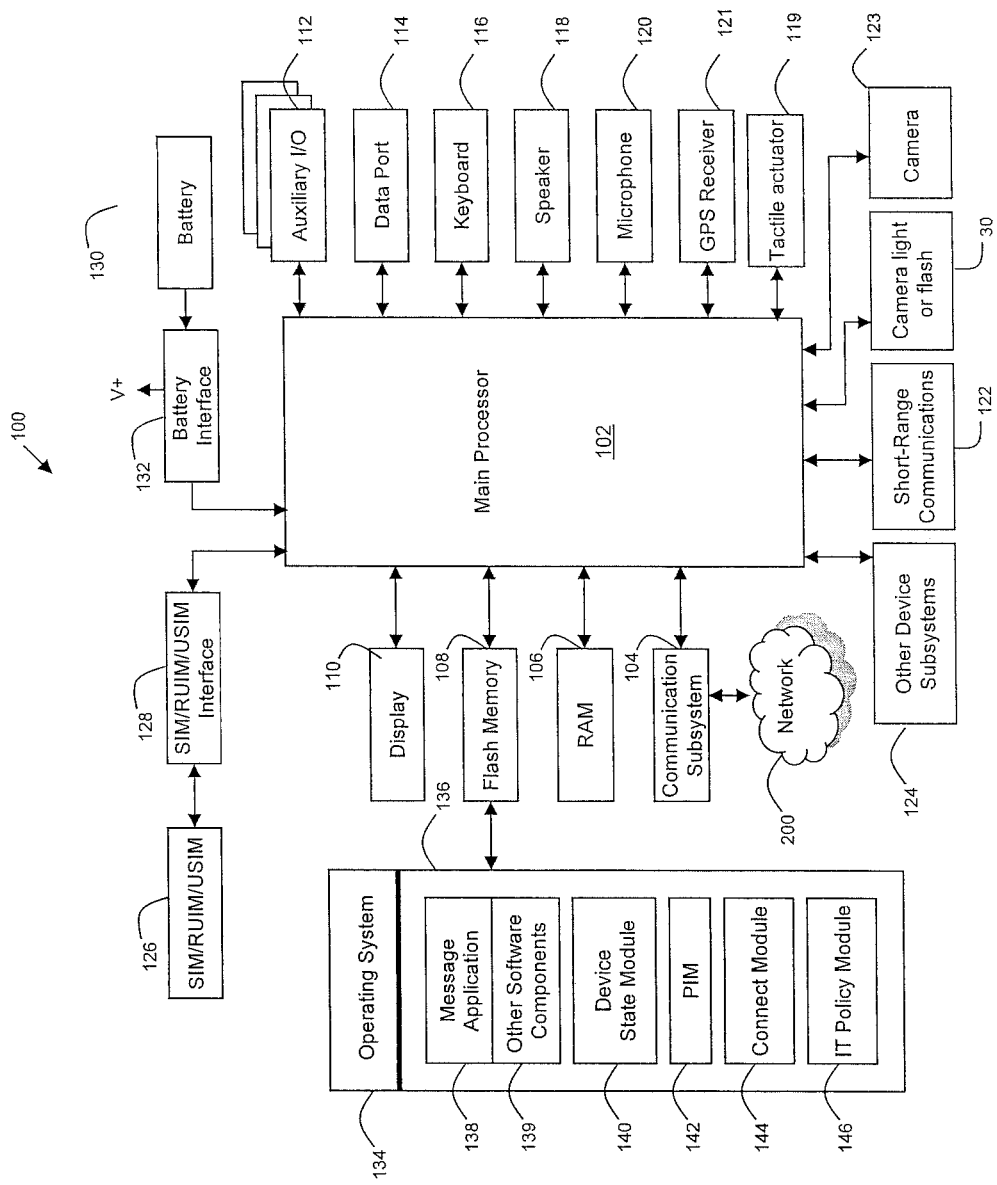
FIG. 5 is a block diagram of an example embodiment mobile device.

Referring first to FIG. 5, shown therein is a block diagram of an example embodiment of a mobile device 100 which may be used to implement the example embodiments disclosed herein. The mobile device 100 includes a number of components such as a main processor 102 that controls the overall operation of the mobile device 100. Communication functions, including data and voice communications, are performed through a communication subsystem 104. The communication subsystem 104 receives messages from and sends messages to a wireless network 200. In this example embodiment of the mobile device 100, the communication subsystem 104 is configured in accordance with the Global System for Mobile Communication (GSM) and General Packet Radio Services (GPRS) standards, which is used worldwide. Other communication configurations that are equally applicable are the 3G and 4G networks such as EDGE, UMTS and HSDPA, LTE, Wi-Max etc. New standards are still being defined, but it is believed that they will have similarities to the network behaviour described herein, and it will also be understood by persons skilled in the art that the example embodiments described herein are intended to use any other suitable standards that are developed in the future. The wireless link connecting the communication subsystem 104 with the wireless network 200 represents one or more different Radio Frequency (RF) channels, operating according to defined protocols specified for GSM/GPRS communications.

The main processor 102 also interacts with additional subsystems such as a Random Access Memory (RAM) 106, a flash memory 108, a display 110, an auxiliary input/output (I/O) subsystem 112, a data port 114, a keyboard 116, a speaker 118, a microphone 120, a GPS receiver 121, short-range communications 122, a camera 123, a camera light or flash 30, and other device subsystems 124.

The mobile device 100 includes an actuator 119 that can create a tactile response. For example, the actuator is a vibrator that creates a vibrating feel.

Some of the subsystems of the mobile device 100 perform communication-related functions, whereas other subsystems may provide "resident" or on-device functions. By way of example, the display 110 and the keyboard 116 may be used for both communication-related functions, such as entering a text message for transmission over the network 200, and device-resident functions such as a calculator or task list.

The mobile device 100 can send and receive communication signals over the wireless network 200 after required network registration or activation procedures have been completed. Network access is associated with a subscriber or user of the mobile device 100. To identify a subscriber, the mobile device 100 may use a subscriber module component or "smart card" 126, such as a Subscriber Identity Module (SIM), a Removable User Identity Module (RUIM) and a Universal Subscriber Identity Module (USIM). In the example shown, a SIM/RUIM/USIM 126 is to be inserted into a SIM/RUIM/USIM interface 128 in order to communicate with a network. Without the component 126, the mobile device 100 is not fully operational for communication with the wireless network 200. Once the SIM/RUIM/USIM 126 is inserted into the SIM/RUIM/USIM interface 128, it is coupled to the main processor 102.

The mobile device 100 is a battery-powered device and includes a battery interface 132 for receiving one or more rechargeable batteries 130. In at least some example embodiments, the battery 130 can be a smart battery with an embedded microprocessor. The battery interface 132 is coupled to a regulator (not shown), which assists the battery 130 in providing power V+ to the mobile device 100. Although current technology makes use of a battery, future technologies such as micro fuel cells may provide the power to the mobile device 100.

The mobile device 100 also includes an operating system 134 and software components 136 to 146 which are described in more detail below. The operating system 134 and the software components 136 to 146 that are executed by the main processor 102 are typically stored in a persistent store such as the flash memory 108, which may alternatively be a read-only memory (ROM) or similar storage element (not shown). Those skilled in the art will appreciate that portions of the operating system 134 and the software components 136 to 146, such as specific device applications, or parts thereof, may be temporarily loaded into a volatile store such as the RAM 106. Other software components can also be included, as is well known to those skilled in the art.

The subset of software applications 136 that control basic device operations, including data and voice communication applications, may be installed on the mobile device 100 during its manufacture. Software applications may include a message application 138, a device state module 140, a Personal Information Manager (PIM) 142, a connect module 144 and an IT policy module 146. A message application 138 can be any suitable software program that allows a user of the mobile device 100 to send and receive electronic messages, wherein messages are typically stored in the flash memory 108 of the mobile device 100. A device state module 140 provides persistence, i.e. the device state module 140 ensures that important device data is stored in persistent memory, such as the flash memory 108, so that the data is not lost when the mobile device 100 is turned off or loses power. A PIM 142 includes functionality for organizing and managing data items of interest to the user, such as, but not limited to, e-mail, contacts, calendar events, and voice mails, and may interact with the wireless network 200. A connect module 144 implements the communication protocols that are required for the mobile device 100 to communicate with the wireless infrastructure and any host system, such as an enterprise system, that the mobile device 100 is authorized to interface with. An IT policy module 146 receives IT policy data that encodes the IT policy, and may be responsible for organizing and securing rules such as the "Set Maximum Password Attempts" IT policy.

Other types of software applications or components 139 can also be installed on the mobile device 100. These software applications 139 can be pre-installed applications (i.e. other than message application 138) or third party applications, which are added after the manufacture of the mobile device 100. Examples of third party applications include games, calculators, utilities, video chat applications, etc.

The additional applications 139 can be loaded onto the mobile device 100 through at least one of the wireless network 200, the auxiliary I/O subsystem 112, the data port 114, the short-range communications subsystem 122, or any other suitable device subsystem 124.

The data port 114 can be any suitable port that enables data communication between the mobile device 100 and another computing device. The data port 114 can be a serial or a parallel port. In some instances, the data port 114 can be a USB port that includes data lines for data transfer and a supply line that can provide a charging current to charge the battery 130 of the mobile device 100.

For voice communications, received signals are output to the speaker 118, and signals for transmission are generated by the microphone 120. Although voice or audio signal output is accomplished primarily through the speaker 118, the display 110 can also be used to provide additional information such as the identity of a calling party, duration of a voice call, or other voice call related information.

The display 110 can also be used in combination with the camera 123 to provide video chatting capability. It can be appreciated that the mobile device 100 may include more than one camera 123. For example, a front-facing camera, a back-facing camera, or both, may be used to engage in a video chatting session. It can also be appreciated that the camera 123 may be an external hardware component operably connected to the mobile device 100 through the auxiliary I/O 112 or the data port 114.

Figure 6:
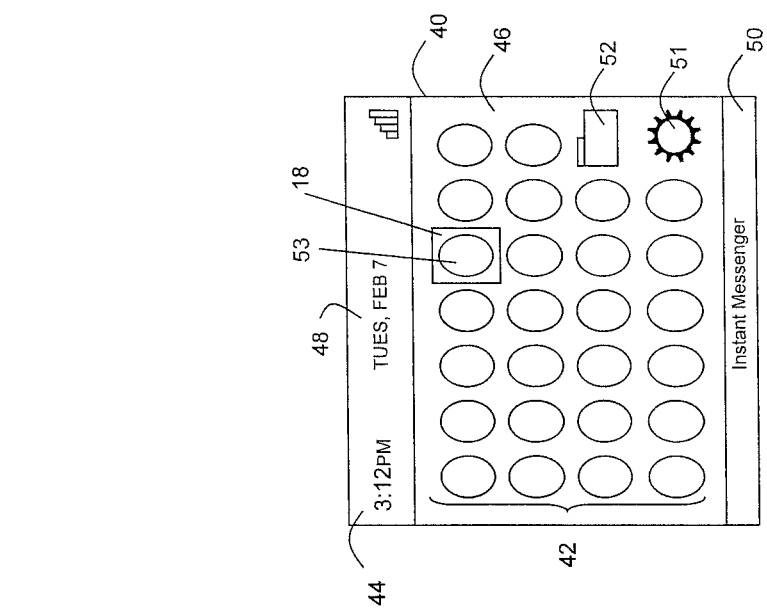
FIG. 6 is a screen shot of a home screen displayed by a mobile device, according to an example embodiment.

Turning now to FIG. 6, the mobile device 100 may display a home screen 40, which can be set as the active screen when the mobile device 100 is powered up and may constitute the main ribbon application. The home screen 40 generally includes a status region 44 and a theme background 46, which provides a graphical background for the display 12. The theme background 46 displays a series of icons 42 in a predefined arrangement on a graphical background. In some themes, the home screen 40 may limit the number of icons 42 shown on the home screen 40 so as to not detract from the theme background 46, particularly where the background 46 is chosen for aesthetic reasons.

The theme background 46 shown in FIG. 6 provides a grid of icons. It will be appreciated that preferably several themes are available for the user to select and that any applicable arrangement may be used. An example icon may be a settings icon 51 used to indicate the capability of changing settings for an application, such as the accessibility application 208. One or more of the series of icons 42 is typically a folder 52 that itself is capable of organizing any number of applications therewithin.

The status region 44 in this example embodiment includes a date/time display 48. The theme background 46, in addition to a graphical background and the series of icons 42, also includes a status bar 50. The status bar 50 provides information to the user based on the location of the selection cursor 18, e.g. by displaying a name for the icon 53 that is currently highlighted.

An application, such as message application 138 may be initiated (opened or viewed) from display 12 by highlighting a corresponding icon 53 using the positioning device 14 and providing a suitable user input to the mobile device 100. For example, message application 138 may be initiated by moving the positioning device 14 such that the icon 53 is highlighted by the selection box 18 as shown in FIG. 6, and providing a selection input, e.g. by pressing the trackball 14*b*.

Figure 7:
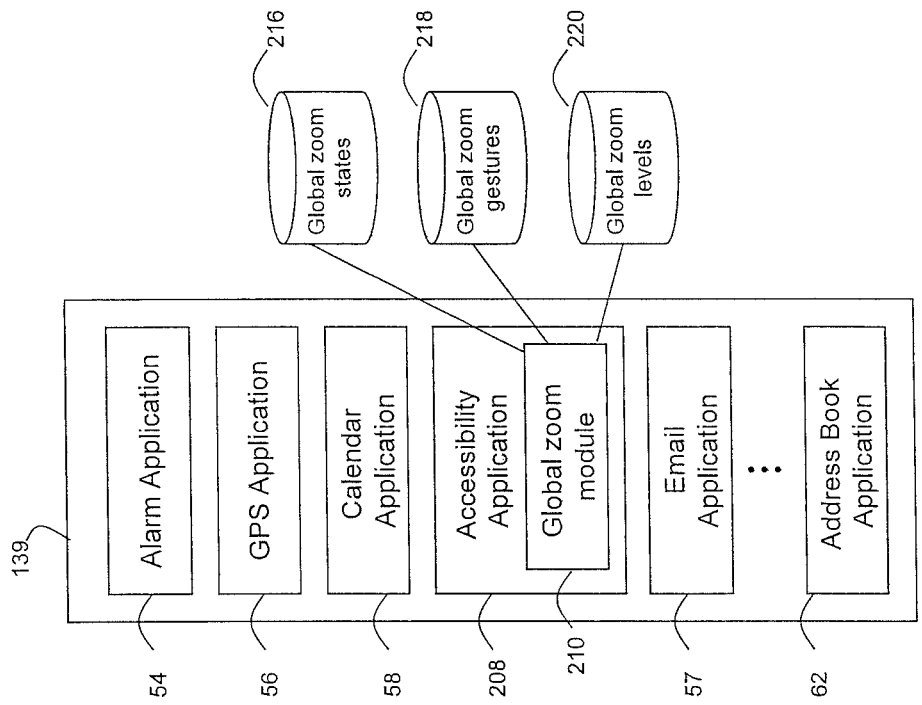
FIG. 7 is a block diagram illustrating example embodiments of the other software applications and components shown in FIG. 5.

FIG. 7 shows an example of the other software applications and components 139 that may be stored and used on the mobile device 100. Only examples are shown in FIG. 7 and such examples are not to be considered exhaustive. In this example, an alarm application 54 may be used to determine alarm settings. A GPS application 56 may be used to determine the location of a mobile device. A calendar application 58 may be used to organize appointments. Another application shown is an email application 57 that may be used to send and receive emails. Another application shown is an address book 62 that is used to store contact information which may include, for example, an email address, a name, and a phone number.

Another example application is the accessibility application 208, including the global zoom module 210. The global zoom module 210, in an example embodiment, is in communication with a database 216 including global zoom states, a database 218 including global zoom gestures, and a database 220 including global zoom levels.

Global zoom states include whether global zoom is turned on or off. In another example embodiment, it also includes whether global zoom is active, or not. Global zoom gestures include various gestures relating to controlling global zoom. In an example embodiment, the gestures are touch screen gestures. Global zoom levels include default zoom settings and saved global zoom settings. In an example embodiment, the saved global zoom settings are provided by a user.

It will be appreciated that any module or component exemplified herein that executes instructions or operations may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data, except transitory propagating signals per se. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the electronic device 100, or accessible or connectable thereto. Any application or module herein described may be implemented using computer readable/executable instructions or operations that may be stored or otherwise held by such computer readable media.

In an example embodiment, a method performed by an electronic device is provided to manage zooming. It includes: receiving an input to increase or decrease a zoom in an application; determining if the application includes a local zoom; if so, determining if a global zoom is turned on; and, if so, turning off the global zoom and increasing or decreasing the zoom using the local zoom.

In an example embodiment, the method further includes receiving an input to turn on the global zoom; and turning on the global zoom. In an example embodiment, a graphical user interface (GUI) is provided to receive the input to turn on the global zoom and to receive an input to turn off the global zoom. In an example embodiment, the application determines if the global zoom is turned on by receiving a value from a global zoom module indicating whether the global zoom is turned on or turned off. In an example embodiment, if the application does not include the local zoom, the method includes increasing or decreasing the zoom using the global zoom. In an example embodiment, after detecting the zoom is increased to a maximum zoom level using the global zoom, the method further includes activating a tactile alert. In an example embodiment, if the global zoom is turned off, the method includes increasing or decreasing the zoom using the local zoom.

Figure 8:
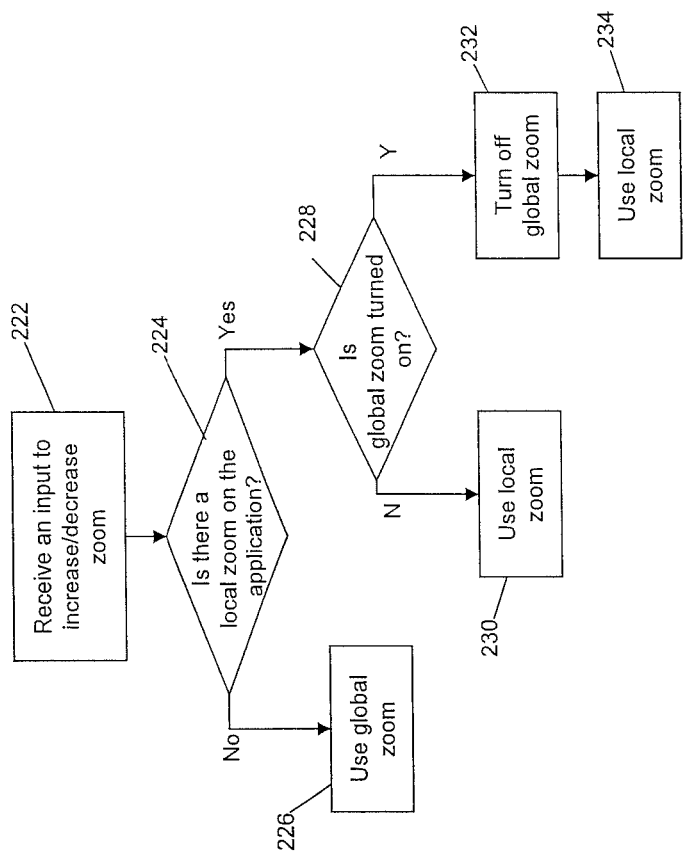
FIG. 8 is a flow diagram of computer executable or processor implemented instructions for determining to use global zoom or local zoom.

Turning to FIG. 8, an example embodiment of computer executable or processor implemented instructions is provided for managing global zoom and local zoom. At block 222, the electronic device 100 receives an input to increase or decrease the zoom, or zoom level. At block 224, the device 100 determines if there is a local zoom functionality on the application. If not, at block 226, global zoom is used. If the application does have local zoom, at block 228, it is determined if the global zoom is turned on.

In an example embodiment, the application can send a request to the accessibility application 208 to determine the state of global zoom. The accessibility application 208 then retrieves a value from the database 216 which indicates whether or not the global zoom is turned on. The accessibility application 208 returns the value to the application.

If it is determined that global zoom is not turned on (e.g. turned off), then local zoom is used to increase or decrease the zoom (block 230). Otherwise, the global zoom is turned off (block 232) and local zoom is used to increase or decrease the zoom (block 234).

In an example embodiment, the application sends a message to the global zoom module 210 to turn off global zoom. The turned-off state of the global zoom is updated in the database 216.

In an example embodiment, it can be appreciated that the global zoom setting can be turned on and off using a GUI. This is described in further detail with respect to FIG. 11.

In some other example embodiments, there is state in which the global zoom is turned on, and within that state, there are further states in which global zoom is activated or not activated. In other words, global zoom can be turned on, but may not be activated. In another state, global zoom can be turned on, and is also activated. However, if global zoom is turned off, global zoom cannot be activated.

If global zoom is activated, the zooming functionality behaves according to the global zoom module 210. If global zoom is not activated, other zooming (e.g. local zoom), or no zooming, functionality is used.

Figure 9:
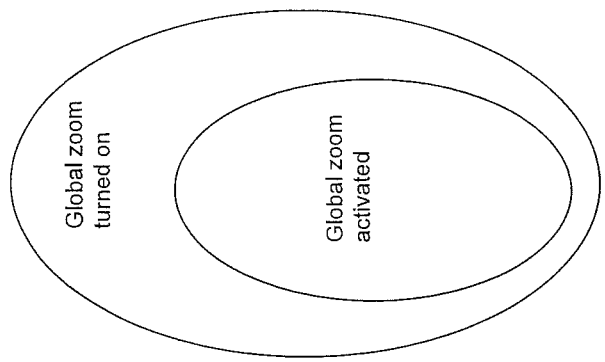
FIG. 9 is an illustration of the relationship between the states of global zoom being turned on and global zoom being activated.

Turning to FIG. 9, an illustration shows the relationship between the state in which global zoom is turned on and the state in which global zoom is active. In particular, encompassed within the state defined by global zoom being turned on are the states defined by global zoom being activated, and global zoom being deactivated.

In an example embodiment, a method performed by an electronic device 100 is provided to manage zooming. It includes: receiving an input to activate global zoom; determining if the global zoom is turned on; and if so, activating the global zoom.

In an example embodiment, the method further includes: before receiving the input activate the global zoom, receiving an input to turn on the global zoom; and turning on the global zoom. In an example embodiment, a GUI is provided to receive the input to turn on the global zoom and to receive an input to turn off the global zoom. In an example embodiment, if the global zoom is not turned on, the global zoom is not activated. In an example embodiment, the input to activate global zoom includes detecting two fingers swiping a touch screen of the electronic device downwards from a top area of the touch screen. In an example embodiment, the method includes: after activating the global zoom, detecting two fingers swiping a touch screen of the electronic device; and panning a viewport in a direction of the two fingers swipe. In an example embodiment, the method includes: after detecting a zoom is increased to a maximum zoom level using the global zoom, activating a tactile alert. In an example embodiment, the global zoom applies to a plurality of applications on the electronic device. In an example embodiment, at least one of the plurality of applications includes a local zoom. In an example embodiment, the method includes: receiving an input to increase or decrease a zoom in an application; determining if the application includes a local zoom; if so, determining if the global zoom is activated; if so, deactivating the global zoom and increasing or decreasing the zoom using the local zoom. In an example embodiment, after detecting the global zoom is activated, displaying a prompt to use the local zoom or the global zoom; if an input associated with the prompt is received to use the local zoom, deactivating the global zoom and increasing or decreasing the zoom using the local zoom. In an example embodiment, the method further includes: if an input associated with the prompt is received to use the global zoom, increasing or decreasing the zoom using the global zoom. In an example embodiment, the method includes: after determining the global zoom is turned on, determining if there is a saved global zoom setting; and if so, using the global zoom to increase or decrease the zooming to the saved global zoom setting. In an example embodiment, the saved global zoom setting was saved during a previous use of the global zoom.

Figure 10:
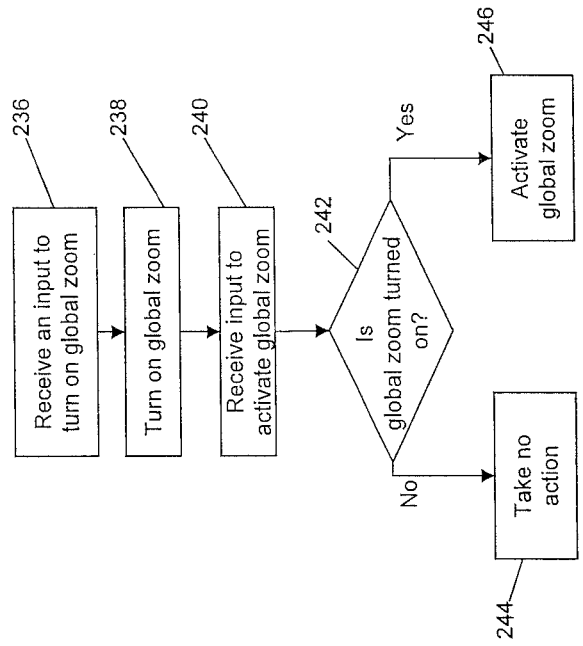
FIG. 10 is a flow diagram of computer executable or processor implemented instructions for activating global zoom.

Turning to FIG. 10, an example embodiment of computer executable or processor implemented instructions is provided for activating global zoom.

At block 236, the electronic device 100 receives an input to turn on global zoom. At block 238, the global zoom functionality is turned on. At block 240, the electronic device 100 receives an input to activate global zoom. At block 242, it is determined if the global zoom is turned on. If not, at block 244, no action is taken. If global zoom is turned on, at block 246, global zoom is activated.

Figure 11:
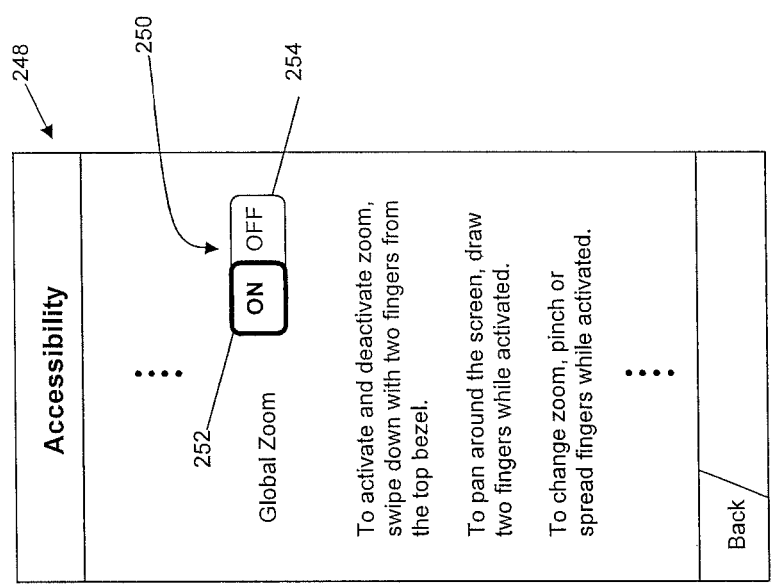
FIG. 11 is a screen shot of an example embodiment graphical user interface (GUI) for turning on and off global zoom.

Turning to FIG. 11, an example embodiment of a GUI 248 is provided for turning on and turning off global zoom. The GUI 248 can be accessed through the accessibility application 208. In an example embodiment, selecting the icon 51 can lead to the display of the GUI 248. The GUI 248 includes a control 250 for turning on and off the global zoom. In FIG. 11, the control 250 shows that the "on" state 252 is currently selected. However, selecting the control 250 would change the global zoom state to "off" 254.

In an example embodiment, the GUI 248 is used to control the on and off states that are stored in the database 216.

When global zoom is turned on, a number of gestures can be used to control zooming and panning. Such gestures can be stored, for example, in the database 218. Example embodiments of such gestures include those for activating global zoom, increasing or decreasing zoom, panning the viewport, and deactivating global zoom.

Figure 12:
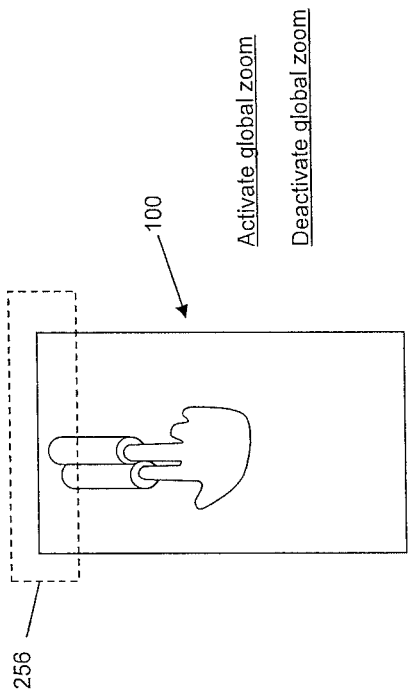
FIG. 12 is an example embodiment of a touch screen gesture for activating global zoom.

Turning to FIG. 12, an example embodiment of a gesture is shown for activating global zoom. In other words, it is an example embodiment of an input used to activate global zoom. It includes detecting two fingers swiping downwards from a top area 256 of a touch screen display on the electronic device 100. In an example embodiment of the mobile device 100c shown in FIG. 4, the top area 256 includes the top area of the touch sensitive non-display area 125. In another example embodiment, another gesture is used to activate the global zoom. In some example embodiments, the same gesture is used to also deactivate global zoom. In other words, using two fingers to swipe downwards from the top area can be used to activate global zoom and, if the gesture is repeated, can be used to deactivate global zoom.

Figure 13:
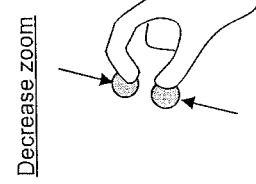
FIG. 13 is an example embodiment of a touch screen gesture for decreasing the zoom.

Turning to FIG. 13, an example embodiment of a pinching gesture is shown, which is used to decrease the zoom level. For example, it zooms out of the image.

Figure 14:
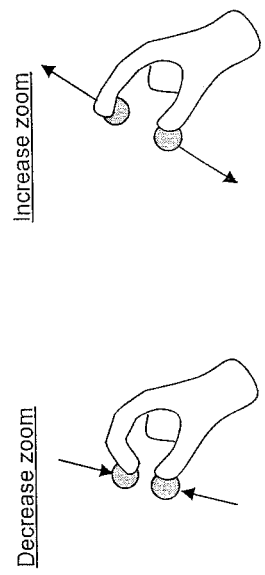
FIG. 14 is an example embodiment of a touch screen gesture for increasing the zoom.

Turning to FIG. 14, an example embodiment of a gesture of two fingers spreading apart, thereby increasing the zoom level. For example, use of such a gesture zooms into the image.

Turning to FIG. 15, an example embodiment of a two finger swipe is used to pan a viewport. In an example embodiment, the viewport is a viewing area, or the visible portion of a 2D area. In some example embodiments, the 2D area is a different size compared to the display screen, for example when increasing or decreasing the zoom level. The viewport can be panned in different directions. The viewport is panned while global zoom is active. In an example embodiment, if global zoom is not activated and a user uses the two finger swipe shown in FIG. 15, that gesture may not lead to any action, or may cause another action different from panning the viewport.

Turning to FIG. 16, an example embodiment of a two finger downwards swipe to the bottom area 257 of the touch screen display is shown. In an example embodiment, this gesture is used to deactivate global zoom.

Other gestures may be used to control the zooming.

Turning to FIG. 17, an example embodiment of computer executable or processor implemented instructions are provided for adjusting zoom to a saved global zoom setting. At block 258, an input is received to activate global zoom. At block 260, it is determined if global zoom is turned on. If not, no action is taken (block 262). At block 264, if global zoom is turned on, it is determined if there is a previously saved global zoom setting. If not, at block 266, the zoom of the image is automatically adjusted on the display screen to a default global zoom setting. If there is a saved global zoom setting, at block 268, the zoom of the image on the display screen is adjusted to the saved global zoom setting. Both the default and saved global zoom settings can be stored in the database 220.

Turning to FIG. 18, an example embodiment of computer executable or processor implemented instructions is provided for saving a global zoom setting, which can be retrieved later for use, such as described in FIG. 17.

At block 270, global zoom is activated. At block 272, the electronic device 100 receives an input to increase or decrease global zoom. The global zoom setting is accordingly increased or decreased. At block 274, an input is received to close an application, within which global zoom was activated. Or, an input is received to deactivate global zoom. At block 276, the current global zoom setting is saved, for example, in the database 220. The global zoom setting may be a percentage representing the magnification increase or decrease. The application is then closed, or the global zoom is then deactivated.

In other words, the last saved global zoom setting that a user has selected is used next time when global zoom is re-activated. For example, if the global zoom setting is at 320% when an application is closed, or the global zoom is deactivated, then next time when the global zoom is reactivated, the application will automatically zoom the image to 320% magnification.

In an example embodiment, the global zoom setting is saved with respect to a given application. In other words, each application has an associated global zoom setting. For example, in a first application, a saved global zoom setting is 150%. In a second application, a saved global zoom setting is 300%. Therefore, when next activating global zoom in the first application, the image on the screen is zoomed into by 150%. When switching applications to the second application, global zoom may not be activated. If activating global zoom in the second application, the global zoom setting is used to zoom in by 300%.

Turning to FIG. 19, in an example embodiment, screen shots 278a and 278b show the automatic zooming process when activating global zoom. In the screen shot 278a, an image of a person 280a and an image 282a of another person are shown. The screen shot 278a also includes a status bar 279a, which shows battery power, time, and connectivity. The images in the screen shot 278a are shown at 100% of their original size. An input 284 is received for activating the global zoom. In the example embodiment, the input 284 includes detecting two fingers swiping the touch screen from the top area of the device.

After detecting the input 284, the global zoom is activated and the images are automatically zoomed into using the saved global zoom setting. As can be seen in the screen shot 278b, the images 280b and 282b are larger than their counterparts 280a and 282a. Similarly, the status bar 279b is larger than its counterpart 279a.

Turning to FIG. 20, an example embodiment of panning is provided. Upon detecting a two finger swipe 286 in the screen shot 278b while global zoom is activated, the electronic device 100 moves the viewport in the same direction as the swipe. The screen shot 278c is shown with the image translated or panned towards one side.

Figure 21:
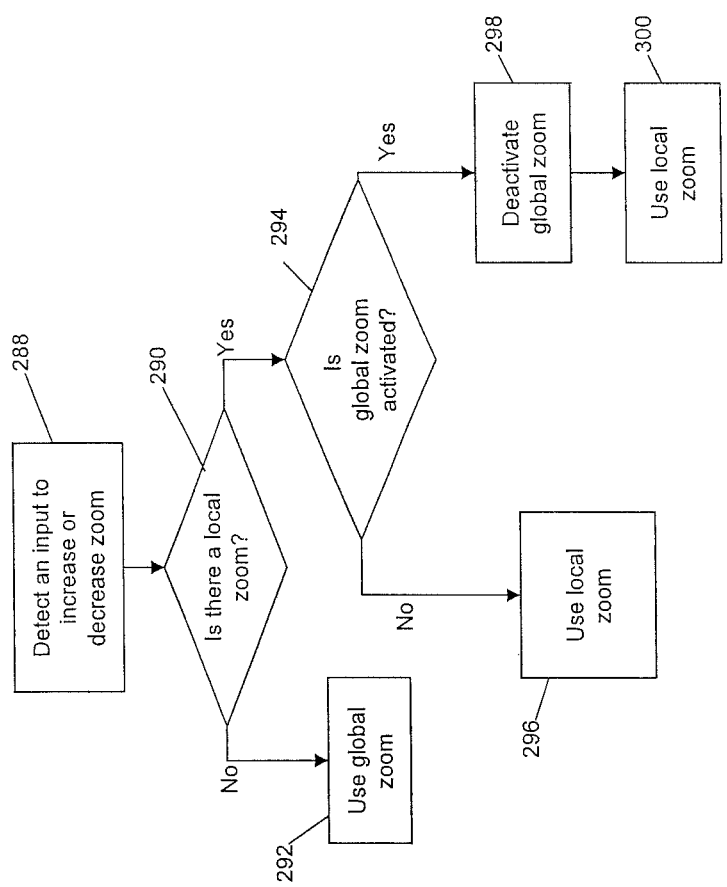
FIG. 21 is a flow diagram of computer executable or processor implemented instructions for determining to use global zoom or local zoom.

Turning to FIG. 21, an example embodiment of computer executable or processor implemented instructions is provided for determining whether to use local zoom or global zoom. In this example embodiment, even if global zoom is active, local zoom is used to override the global zoom. This can be useful if local zoom offers better rendering of details when zooming into an image.

It can be appreciated that, in some example embodiments, local zoom algorithms of an application interact with the content being displayed by the application. By using information about the type of content (e.g. font, text data, image data, color variation, size, shape, etc.), a greater amount of detail can be displayed when zooming into content with local zoom.

In an example embodiment, global zoom is generic and unaware of the details of the content being displayed. The zooming capability of global zoom operates by enlarging the image shown on the display screen. Therefore, in some cases, it may be preferred to use local zoom over global zoom in order to show more detail.

Continuing with FIG. 21, at block 288, an input to increase or decrease zoom is detected within an application. In an example embodiment, the input is a pinching or spreading gesture using two fingers on a touch screen. At block 290, the electronic device 100 determines if there is local zoom functionality on the application. If not, global zoom is used (block 292). If there is local zoom functionality on the application, at block 294, the electronic device determines if the global zoom functionality is currently activated. If not, at block 296, the local zoom is used. It the global zoom is activated, at block 298, it is deactivated. The local zoom functionality is then used to increase or decrease the zoom level according to the input.

In another example embodiment, an option is provided to select between local zoom or global zoom. In another example embodiment, global zoom is used to override local zoom. This may be useful if a user would like all the content on the display screen to be enlarged. For example, local zoom may in some cases only zoom in and out of certain content, but leave other content size the same.

Figure 22:
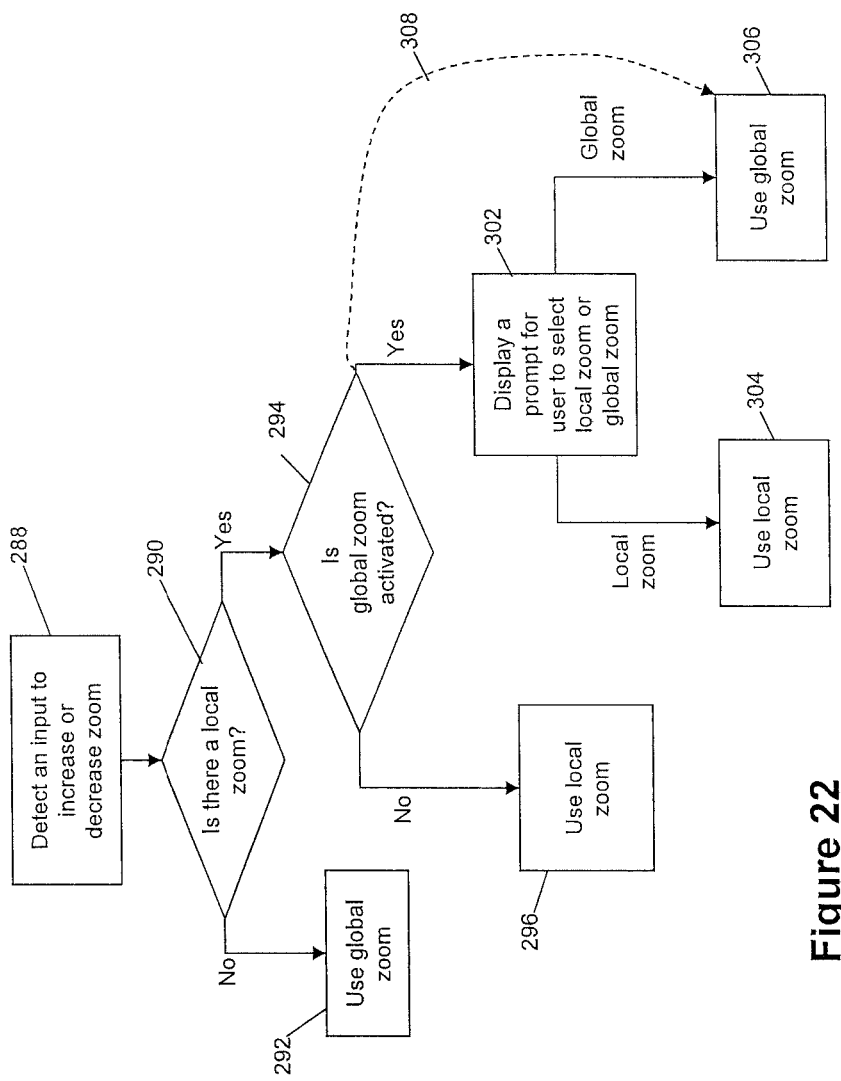
FIG. 22 is a flow diagram of computer executable or processor implemented instructions for determining to use global zoom or local zoom.

Turning to FIG. 22, an example embodiment of computer executable or processor implemented instructions is provided for selecting between local and global zoom. Blocks 288, 280, 292, 294 and 296 are implemented, and they are described earlier with respect to FIG. 21. If global zoom is activated, as per block 294, then at block 302, a prompt is displayed for the user to select local zoom or global zoom. If local zoom is selected, as per the prompt, then local zoom is used to increase or decrease the zoom (block 304). If global zoom is selected, then global zoom is used to increase or decrease the zoom (block 306).

In another example embodiment, upon determining that the global zoom is activated, as per dotted line 308, the process automatically continues using the global zoom (block 306). In other words, there is no prompt.

Turning to FIG. 23, an example screen shot 310 is shown including a prompt GUI 312. The prompt, for example, can be a pop-up display. The prompt includes controls 314 and 316 for selecting one of global zoom and local zoom.

The prompt GUI 312 can also include an option 317 to remember the user's selection. For example, if the user selects or checks-off the option 317 and selects the control 314 for global zoom, in future instances global zoom will be used. For example, referring briefly back to FIG. 22, at block 294, after determining that global zoom is activated, the electronic device 100 will automatically select global zoom (block 306) according to the previously saved setting as per the user. The prompt will not be initiated.

Similarly, if the user selects the option 317 to save the setting, and also selects local zoom, then local zoom will be used in future instances. For example, referring briefly back to FIG. 22, at block 294, after determining that global zoom is activated, the electronic device 100 will automatically select local zoom (block 304) according to the previously saved setting as per the user. The prompt will not be initiated.

Turning to FIG. 24, an example embodiment of computer executable or processor implemented instructions is provided for selecting global zoom or local zoom. The selected zooming function is shown through an indicator.

At block 318, the electronic device 100 determines if there is local zoom functionality with respect to a given application. If not, no action is taken (block 320). If so, at block 322, an indicator is displayed that one of global zoom and local zoom is currently active. At block 324, an input is received to select the other one of global zoom and local zoom. At block 326, the other one of global zoom and local zoom is activated over the one of global zoom and local zoom. At block 328, the electronic device displays an indicator that the other one of global zoom and local zoom is activated.

Figure 25:
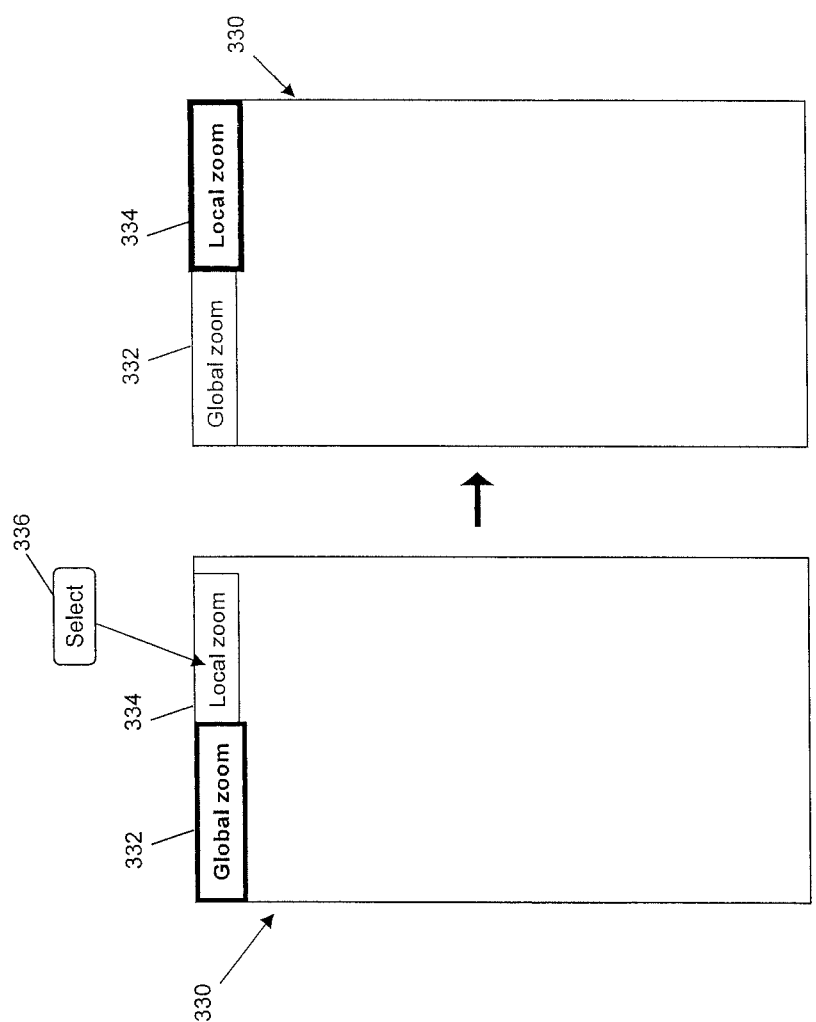
FIG. 25 is an illustration of example embodiment screen shots of a GUI for selecting global zoom or local zoom.

Turning to FIG. 25, an example embodiment of a screen shot 330 is provided for selecting between global zoom and local zoom. The screen shot 330 in an application includes controls 332 and 334 for selecting global zoom and local zoom, respectively. In this example, as indicated by the bold text and darkened border, global zoom is currently activated. A user provides an input selection 336 for control 334.

As a result, local zoom is then activated instead. This is now indicated by the bold text and darkened border around the control 334. Other types of indicators and controls can be used.

In an example embodiment, while using global zoom, if a user increases the global zoom to a maximum global zoom setting, then a tactile alert or response is provided. For example, a vibration is initiated. In an example embodiment, the maximum global zoom setting is 500%. In another example embodiment, a tactile alert or response is provided when a minimum global zoom setting is reached. The tactile feedback lets the user know that the maximum or minimum level of the global zoom is reached.

The steps or operations in the flow charts described herein are just for example. There may be many variations to these steps or operations without departing from the spirit of the invention or inventions. For instance, the steps may be performed in a differing order, or steps may be added, deleted, or modified.

The GUIs and screen shots described herein are just for example. There may be variations to the graphical and interactive elements without departing from the spirit of the invention or inventions. For example, such elements can be positioned in different places, or added, deleted, or modified.

It will be appreciated that the particular example embodiments shown in the figures and described above are for illustrative purposes only and many other variations can be used according to the example embodiments described. Although the above has been described with reference to certain specific example embodiments, various modifications thereof will be apparent to those skilled in the art as outlined in the appended claims.

The invention claimed is:

1. A method performed by an electronic device, to manage zooming, comprising:
receiving, within an application executing on an operating system, a touch input from a touch enabled screen to increase or decrease a zoom setting in an application;
automatically determining if the application includes a local zoom function that is separate from a global zoom function,
the global zoom function provided by a separate module that is separate from the application and increasing or decreasing a size of all information presented on the touch enabled screen,
the local zoom function provided by the application and increasing or decreasing a size of content displayed by the application;
based on determining that the application includes the local zoom function, automatically determining, within the application, that the global zoom function is activated; and
based on determining that the global zoom function is activated, the application automatically turning off the global zoom function of the separate module and increasing or decreasing the size of content displayed by the application using the local zoom function.

2. The method of claim 1 further comprising:
after increasing or decreasing the size of content displayed by the application using the local zoom function, receiving an input to turn on the global zoom function; and
turning on the global zoom.

3. The method of claim 2 wherein a graphical user interface (GUI) is provided to receive the input to turn on the global zoom function and to receive an input to turn off the global zoom function.

4. The method of claim 1 wherein the application determines if the global zoom function is turned on by receiving a value from a global zoom module indicating whether the global zoom function is turned on or turned off.

5. The method of claim 1 wherein if the application does not include the local zoom function, increasing or decreasing size of all information presented on the touch enabled screen using the global zoom function.

6. The method of claim 5 further comprising, after detecting the zoom setting is increased to a maximum zoom setting using the global zoom function, activating a tactile alert.

7. The method of claim 1 wherein the local zoom function increase or decreases sizing of a portion of content in the application without affecting sizing of a remaining portion of the content in the application.

8. The method of claim 1, further comprising:
prior to the application automatically turning off the global zoom function,
based on receiving the input to increase or decrease the zoom setting and
based on determining that the global zoom function is activated,
presenting a user interface to receive a zoom type input that indicates a selection of one of the local zoom function or the global zoom function; and
based on receiving, in association with the user interface, the zoom type input that indicates the global zoom function, increasing or decreasing the zoom setting using the global zoom function, and
wherein the application automatically turning off the global zoom function and increasing or decreasing the size of content displayed by the application using the local zoom function is further based on receiving the zoom type input that indicates the local zoom function.

9. The method of claim 1, wherein the application executes on the electronic device comprising the screen presenting information subject to the zoom setting, and
wherein the input is received via user input facilities of the electronic device.

10. The method of claim 1, further comprising, based on determining that the global zoom function is not activated, increasing or decreasing the zoom setting using the local zoom function.

11. An electronic device configured to manage zooming, comprising a processor configured to at least:
- receive, within an application executing on an operating system, a touch input from a touch enabled screen to increase or decrease a zoom in an application;
- automatically determining if the application includes a local zoom function that is separate from a global zoom function,
    - the global zoom function provided by a separate module that is separate from the application and increasing or decreasing a size of all information presented on the touch enabled screen,
    - the local zoom function provided by the application and increasing or decreasing a size of content displayed by the application;
- based on determining that the application includes the local zoom function, automatically determine within the application, that the global zoom function is activated; and
- based on determining that the global zoom function is turned on, automatically turn off, by the application, the global zoom function of the separate module and increase or decrease the size of content displayed by the application using the local zoom function.

12. The electronic device of claim 11 wherein the processor is further configured to at least:
- after increasing or decreasing size of content displayed by the application using the local zoom function, receive an input to turn on the global zoom function; and
- turn on the global zoom function.

13. The electronic device of claim 12 wherein the processor is further configured to initiate display of a graphical user interface (GUI) to receive the input to turn on the global zoom function and to receive an input to turn off the global zoom function.

14. The electronic device of claim 11 further comprising a global zoom module, and wherein the application determines if the global zoom function is turned on by receiving a value from the global zoom module indicating whether the global zoom function is turned on or turned off.

15. The electronic device of claim 11 wherein the processor is further configured to, after detecting the zoom setting is increased to a maximum zoom setting using the global zoom function, activate a tactile alert.

16. The electronic device of claim 11 wherein the local zoom function increase or decrease sizing of a portion of content displayed in the application without affecting sizing of a remaining portion of the content displayed in the application.

17. A non-transitory computer readable medium comprising executable instructions performed by an electronic device to manage zooming, the instructions comprising:
- receiving, within an application executing on an operating system, a touch input from a touch enabled screen to increase or decrease a zoom setting in an application;
- automatically determining if the application includes a local zoom function that is separate from a global zoom function,
    - the global zoom function provided by a separate module that is separate from the application and increasing or decreasing a size of all information presented on the touch enabled screen,
    - the local zoom function provided by the application and increasing or decreasing a size of content displayed by the application;
- based on determining that the application includes the local zoom function, automatically determining, within the application, that the global zoom function is activated; and
- based on determining that the global zoom function is activated, the application automatically turning off the global zoom function of the separate module and increasing or decreasing the size of content displayed by the application using the local zoom function.

18. The non-transitory computer readable medium of claim 17, wherein the instruction further comprise:
- after increasing or decreasing size of content displayed by the application using the local zoom function, receiving an input to turn on the global zoom function; and
- turning on the global zoom function.

19. The non-transitory computer readable medium of claim 18 wherein the instructions further comprise providing a graphical user interface (GUI) to receive the input to turn on the global zoom function and to receive an input to turn off the global zoom function.

20. The non-transitory computer readable medium of claim 17 wherein the application determines if the global zoom function is turned on by receiving a value from a global zoom module indicating whether the global zoom function is turned on or turned off.

21. The non-transitory computer readable medium of claim 17 wherein if the application does not include the local zoom function, the instructions further comprise increasing or decreasing size of all information presented on the touch enabled screen using the global zoom function.

* * * * *